United States Patent [19]

Marinak et al.

[11] Patent Number: 4,517,369

[45] Date of Patent: May 14, 1985

[54] PREPARATION OF MIXTURES RICH IN 3,4,5,6-TETRACHLORO-2-TRICHLOROMETHYL PYRIDINE

[75] Inventors: Michael J. Marinak, Kelso; John L. Simonson, Longview, both of Wash.

[73] Assignee: Kalama Chemical, Inc., Kalama, Wash.

[21] Appl. No.: 426,916

[22] Filed: Sep. 29, 1982

[51] Int. Cl.$^3$ .............................................. C07D 213/61
[52] U.S. Cl. ...................................... 546/345; 546/327
[58] Field of Search .......................................... 546/345

[56] References Cited

U.S. PATENT DOCUMENTS

| | | | |
|---|---|---|---|
| 3,186,994 | 6/1965 | Johnston et al. | 546/345 |
| 3,234,229 | 2/1966 | Redemann | 546/345 |
| 3,256,167 | 6/1966 | Norton et al. | 546/345 |
| 3,418,323 | 12/1968 | Johnston et al. | 546/345 |
| 4,227,001 | 10/1980 | Dietsche et al. | 546/345 |
| 4,256,894 | 3/1981 | Dietsche | 546/345 |

FOREIGN PATENT DOCUMENTS 957276  5/1964  United Kingdom ............... 546/345

OTHER PUBLICATIONS

Kosorotov et al., Kinetika i Kataliz, vol. 19, No. 6, pp. 1393–1398, (Nov.–Dec. 1978), (English Translation).

*Primary Examiner*—Henry R. Jiles
*Assistant Examiner*—Robert C. Whittenbaugh
*Attorney, Agent, or Firm*—Graybeal & Cullom

[57] ABSTRACT

Preparation of mixtures rich in 3,4,5,6-tetrachloro-2-trichloromethyl pyridine by chlorinating 3,4,5-trichloro-2-trichloromethyl pyridine, 3,5-dichloro-2-trichloromethyl pyridine or 5-chloro-2-trichloromethyl pyridine, or mixtures thereof, in the presence of ferric chloride catalyst in the temperature range of from about 170° C. to about 220° C.

4 Claims, No Drawings

PREPARATION OF MIXTURES RICH IN 3,4,5,6-TETRACHLORO-2-TRICHLOROMETHYL PYRIDINE

BACKGROUND OF THE INVENTION

1. Field of the Invention

The present invention relates to preparation of mixtures rich in 3,4,5,6-tetrachloro-2-trichloromethyl pyridine by chlorination in the presence of ferric chloride catalyst of 3,4,5-trichloro-2-trichloromethyl pyridine, 3,5-dichloro-2-trichloromethyl pyridine or 5-chloro-2-trichloromethyl pyridine, or mixtures thereof. Mixtures rich in 3,4,5,6-tetrachloro-2-trichloromethyl pyridine are useful as intermediates in the preparation of agricultural chemicals, especially herbicides.

2. Description of the Prior Art

The present invention concerns the preparation of mixtures rich in 3,4,5,6-tetrachloro-2-trichloromethyl pyridine by the reaction of 5-chloro, 3,5-dichloro, or 3,4,5-trichloro-2-trichloromethyl pyridine, or mixtures thereof, with gaseous chlorine at temperatures from 170° C. to 220° C. in the presence of ferric chloride catalyst. 3,4,5,6-tetrachloride-2-trichloromethyl pyridine has utility as an intermediate in herbicides such as those described in Redemann U.S. Pat. No. 3,234,229. Norton et al U.S. Pat. No. 3,256,167 describes a process for manufacturing 3,4,5,6-tetrachloro-2-trichloromethyl pyridine by reacting alpha-picoline hydrochloride with chlorine between 95° C. and 120° C. Molar yields of 27% of 3,4,5,6-tetrachloro-2-trichloromethyl pyridine are taught in Johnston et al U.S. Pat. No. 3,418,323 by ultraviolet light catalyzed chlorination of 3,4,5-trichloro-2-trichloromethyl pyridine at 150° C. Johnston et al U.S. Pat. No. 3,186,994 teaches the ultraviolet catalyzed chlorination of 3,4,5-trichloro-2-trichloromethyl pyridine at 250° C. to yield pentachloropyridine. There is no prior disclosure known to applicants which teaches the production of 3,4,5,6-tetrachloro-2-trichloromethyl pyridine by chlorination of 5-chloro or 3,5-dichloro-2-trichloromethyl pyridine.

SUMMARY OF THE INVENTION

It has now been discovered that molar yields in excess of 65% of 3,4,5,6-tetrachloro-2-trichloromethyl pyridine can be obtained by chlorinating 3,4,5-trichloro-2-trichloromethyl pyridine from 170° C. to 220° C. in the presence of ferric chloride catalyst, present in an amount from about ½ to about 7½% by weight. In addition, mixtures rich in 3,4,5,6-tetrachloro-2-trichloromethyl pyridine are obtained by chlorinating 5-chloro or 3,5-dichloro-2-trichloromethyl pyridine in the presence of ferric chloride catalyst at temperatures of from about 170° C. to about 220° C.

The ferric chloride concentration, temperature and residence time are key variables in optimizing the yield of 3,4,5,6-tetrachloro-2-trichloromethyl pyridine. Other Lewis acid catalysts such as aluminum chloride and zinc chloride were tested in the chlorination of 3,4,5-trichloro-2-trichloromethyl pyridine but their molar yields were about 30 to 35% 3,4,5,6-tetrachloro-2-trichloromethyl pyridine versus the 27% described in Johnston et al U.S. Pat. No. 3,418,323.

Mixtures containing molar yields in excess of 65% of 3,4,5,6-tetrachloro-2-trichloromethyl pyridine based on conversion of 3,4,5-trichloro-2-trichloromethyl pyridine have been achieved. Various ferric chloride concentrations have been explored and molar yields of 3,4,5,6-tetrachloro-2-trichloromethyl pyridine (based on 3,4,5-trichloro-2-trichloromethyl pyridine conversion) of 48% at one-half weight percent ferric chloride to greater than 65% at greater than 3% ferric chloride at temperatures of 200° C. to 210° C. have been achieved. Other Lewis acid catalysts such as zinc chloride and aluminum chloride resulted in only 30 to 35% molar yields of 3,4,5,6-tetrachloro-2-trichloromethyl pyridine. These yields amount to only a slight improvement over ultraviolet light-catalyzed yields of 27%.

DESCRIPTION OF THE PREFERRED EMBODIMENTS

Example 1

A bath liquid phase chlorination appears to be the best mode of operation in order to obtain maximum yields of 3,4,5,6-tetrachloro-2-trichloromethyl pyridine. Ferric chloride was the best catalyst tested from a yield standpoint. Ferric chloride concentrations of at least ½% by weight appear to be necessary to give substantially increased yields of 3,4,5,6-tetrachloro-2-trichloromethyl pyridine.

Fifty grams of a mixture respectively containing about 32% 3,4,5-trichloro and about 64% 3,4,5,6-tetrachloro-2-trichloromethyl pyridine on a molar basis were charged to an electrically heated 250 ml glass batch chlorination reactor. 1½ grams of anhydrous ferric chloride powder was charged to the reactor and chlorine at 70 grams/hour was sparged into the reactor through a bottom discharging sparger and the temperature adjusted to 200° C. The flow of chlorine was controlled so that at least a 50% excess of chlorine was present in the vent from the reactor. The reaction was allowed to proceed for 5 hours at which time the optimum yield of 3,4,5,6-tetrachloro-2-trichloromethyl pyridine was obtained at about a 94 molar percent conversion of the 3,4,5-trichloro-2-trichloromethyl pyridine. The main other product produced was pentachloropyridine. The reactor contents were then transferred to a vacuum distillation product recovery section where the lower boiling chlorinated pyridine compounds such as pentachloropyridine were separated from the 3,4,5,6-tetrachloro-2-trichloromethyl pyridine. The molar yield of 3,4,5,6-tetrachloro-2-trichloromethyl pyridine was greater than 65% based on the reacted 3,4,5-trichloro-2-trichloromethyl pyridine. Another separation method involved hydrolyzing the 3,4,5,6-tetrachloro-2-trichloromethyl pyridine resultant mixture in concentrated sulfuric acid, for example, then a chlorinated solvent such as methylene chloride, chloroform, or perchloroethylene can be used to separate the pentachloropyridine from the resultant product of the 3,4,5,6-tetrachloro-2-trichloromethyl pyridine hydrolysis, i.e. 3,4,5,6-tetrachloro picolinic acid Summarizing Example 1, starting with fifty grams of a mixture rich in 3,4,5-trichloro-2-trichloromethyl pyridine, the analysis of which is set forth in Table One, and which contained 3% by weight ferric chloride, its chlorination with 70 grams per hour of chlorine, sparged into a 250 ml glass reactor at 200° C. for 5 hours, resulted in a product the analysis of which is set forth in Table One. As will be noted, a molar yield in excess of 65% of 3,4,5,6-tetrachloro-2-trichloromethyl pyridine based on 3,4,5-trichloro-2-trichloromethyl pyridine conversion was obtained.

Example 2

Fifty grams of chlorinated pyridines rich in 3,4,5-trichloro-2-trichloromethyl pyridine, the analysis of which is set forth in Table Two, were charged to a reactor like that used in Example 1. One and one-half grams of anhydrous ferric chloride were also added to the reactor. Chlorine at a flow rate of 120 grams per hour was sparged into the reactor and the temperature was brought to 220° C. for 2 hours. The results are listed in Table Two. After two hours 61% mole of the 3,4,5-trichloro-2-trichloromethyl pyridine that had reacted was converted to the desired 3,4,5,6-tetrachloro-2-trichloromethyl pyridine.

Example 3

One hundred grams of chlorinated pyridines rich in 3,4,5-trichloro-2-trichloromethyl pyridine, the analysis of which is set forth in Table Three, were charged to the same reactor as used in Example 1. One-half gram of anhydrous ferric chloride was also added to the reactor. Chlorine at a flow rate of 70 grams per hour was sparged into the reactor and the temperature was brought to 210° C. The chlorination continued for 28 hours with the results tabulated in Table Three. The overall molar yield of 3,4,5,6-tetrachloro-2-trichloromethyl pyridine was about 48% based on the 93.6% conversion of 3,4,5-trichloro-2-trichloromethyl pyridine. This yield was less than Example 1 (48% versus 65% yield), indicating that a minimum catalyst concentration exists for optimum yields.

Example 4

One hundred grams of a mixture rich in 3,4,5-trichloro-2-trichloromethyl pyridine, the analysis of which is set forth in Table Four, containing 7.5 weight percent ferric chloride, was chlorinated with about 70 grams per hour of chlorine sparged into the same reactor as used in Example 1 at 200° C. for 12 hours. Table Four lists the results. A molar yield of about 67% was realized, based on the conversion of 3,4,5-trichloro-2-trichloromethyl pyridine.

Example 5

One hundred grams of a mixture rich in 3,5-dichloro, 3,4,5-trichloro-2-trichloromethyl-, and 3,4,5,6-tetrachloro pyridine, the analysis of which is set forth in Table Five, and containing 4% by weight of ferric chloride was chlorinated as in the previous Examples with 70 grams per hour of chlorine at 150° C. for 10 hours and at 200° C. for 20 hours. Table Five lists the results. The chlorination rate at 150° C. was too slow to be of practical use. The concentration of 3,4,5,6-tetrachloro-2-trichloromethyl pyridine increased from about 27 mole percent initially to about 54 mole percent in the final mixtures. The 3,5-dichloro and 3,4,5-trichloro-2-trichloromethyl pyridine went from initial values of about 26 and 34 mole percent to trace quantities in the final mixtures. The overall molar yield of 3,4,5,6-tetrachloro-2-trichloromethyl pyridine from the chlorinated pyridine mixture was about 44%.

Example 6

In a reactor system like that used in Example 1, fifty grams of a chlorinated pyridines mixture which contained about 78% 5-chloro-2-trichloromethyl pyridine, the analysis of which is set forth in Table Six, and containing 3% ferric chloride was chlorinated via a chlorine sparger with 70 grams per hour of chlorine at 200° C. for 28 hours. Table Six lists the results. A yield of about 16% 3,4,5,6-tetrachloro-2-trichloromethyl pyridine, based on a 5-chloro-2-trichloromethyl pyridine conversion, was achieved.

Example 7

Fifty grams of a chlorinated pyridine mixture which contained about 88% 5-chloro-2-trichloromethyl pyridine, 7.4% 6-chloro-2-trichloromethyl pyridine and 3 weight percent ferric chloride was chlorinated as in the previous Examples with seventy grams per hour of sparged chlorine for 12 hours at 220° C. The initial analysis and resulting product analysis are listed in Table Seven.

Example 8

A batch chlorinator was charged with fifty grams of a chloropyridine mixture which contained about 92% 3,5-dichloro-2-trichloromethyl pyridine and 2% ferric chloride by weight. Seventy grams per hour of chlorine was sparged through the reactor for 32 hours at a reactor temperature of 150° C. and 76 hours at a temperature of 175° C. Table Eight lists the results. This Example demonstrates that temperatures below about 170° C. have too slow a rate of chlorination to be practical.

Example 9

To compare the effectiveness of aluminum chloride as the catalyst for the reaction, one hundred grams of chlorinated pyridines containing about 96% 3,4,5-trichloro-2-trichloromethyl pyridine, the analysis of which is set forth in Table Nine, were charged to the same reactor as used in Example 1. One gram of anhydrous aluminum chloride was added. Chlorine at a flow rate of seventy grams/hour was sparged into the chlorinated pyridine liquid and the temperature controlled at 210° C. for 24 hours. Table Five lists the results. More pentachloropyridine was produced with this reaction when compared with the ferric chloride catalyzed reactions of the earlier Examples. A molar yield of about 30% of 3,4,5,6-tetrachloro-2-trichloromethyl pyridine was obtained, based on 3,4,5-trichloro-2-trichloromethyl pyridine conversion.

Example 10

To compare the effectiveness of zinc metal as the catalyst for the reaction, one hundred grams of chlorinated pyridines containing about 96% 3,4,5-trichloro-2-trichloromethyl pyridine was charged to the same reactor as used in Example 1. One gram of thin zinc metal strips was added. Chlorine at a flow rate of seventy grams/hour was sparged into the chlorinated pyridine liquid and the temperature controlled at 210° C. for 32 hours. Table Ten lists the results. A molar yield of about 35% 3,4,5,6-tetrachloro-2-trichloromethyl pyridine was obtained, based on 3,4,5-trichloro-2-trichloromethyl pyridine conversion.

Example 11

To compare the effectiveness of zinc chloride as the catalyst for the reaction, one hundred grams of chlorinated pyridines containing about 96% 3,4,5-trichloro-2-trichloromethyl pyridine were charged to like reactor. One gram of anhydrous zinc chloride was added. Chlorine at a flow rate of 70 grams/hour was sparged into the chlorinated pyridine liquid and the temperature maintained at 210° C. for 26 hours. Table Eleven lists the results. A molar yield of about 35% 3,4,5,6-tetrachloro-2-trichloromethyl pyridine was obtained, based on 3,4,5-trichloro-2-trichloromethyl pyridine conversion.

TABLE ONE

| Compound | Molar % of Initial Charge | Molar % after 5 hrs. @ 200° C. |
|---|---|---|
| 2,3,4,5,6-pentachloropyridine | 2.3% | 10.5% |
| 3,5-dichloro-2-trichloromethyl pyridine | 32.2% | 1.9% |
| 3,4,5-trichloro-2-trichloromethyl pyridine | 64.1% | 85.0% |

TABLE TWO

| Compound | Molar % of Initial Charge | Molar % after 1.5 hrs @ 200° C. | Molar % after 2 hrs @ 220° C. |
|---|---|---|---|
| 3,4,5-trichloro-2-trichloromethyl pyridine | 1.6% | 21.8% | 33.6% |
| 3,5-dichloro-2-trichloromethyl pyridine | 96.2% | 59.4% | 44.1% |
| 2,3,4,5,6-pentachloropyridine | 0.4% | 14.0% | 17.2% |

TABLE THREE

| Compound | Molar % of Initial Charge | Molar % after 28 Hrs @ 210° C. |
|---|---|---|
| 3,4,5-trichloro-2-trichloromethyl pyridine | 1.6% | 45.7% |
| 3,5-dichloro-2-trichloromethyl pyridine | 96.2% | 2.4% |
| 2,3,4,5,6-pentachloropyridine | 0.4% | 46.5% |

TABLE FOUR

| Compound | Molar % of Initial Charge | Molar % after 17 Hrs @ 200° C. |
|---|---|---|
| 3,5-dichloro-2-trichloromethyl pyridine | 57.6% | — |
| 3,4,5-trichloro-2-trichloromethyl pyridine | 7.8% | 49.1% |
| 2,3,4,5,6-pentachloropyridine | 19.7% | 42.0% |

TABLE FIVE

| Compound | Molar % of Initial Charge | Molar % after 8 hrs @ 150° C. | Molar % after +20 hrs @ 200° C. |
|---|---|---|---|
| 2-trichloromethyl pyridine | 1.6 | — | |
| 3-chloro-2-trichloromethyl pyridine (mono-Cl) | 26.6 | 21.3 | — |
| 5-chloro-2-trichloromethyl pyridine | 0.9 | 1.4 | — |
| 3,5-dichloro-2-trichloromethyl pyridine | 4.6 | 6.4 | 9.2 |
| 3,4,5-trichloro-2-trichloromethyl pyridine | 34.1 | 35.7 | — |

TABLE FIVE-continued

| Compound | Molar % of Initial Charge | Molar % after 8 hrs @ 150° C. | Molar % after +20 hrs @ 200° C. |
|---|---|---|---|
| 2,3,6-trichloro-4-(trichloromethyl)pyridine 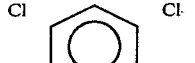 | 27.5 | 30.6 | 54.6 |
| 2,3,5,6-tetrachloropyridine 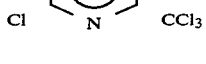 | — | — | 2.5 |
| 2,3,4,6-tetrachloropyridine  | — | — | 20.2 |

TABLE SIX

| Compound | Molar % of Initial Charge | Molar % after 28 hrs. @ 200° C. |
|---|---|---|
| 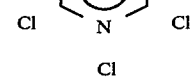 | 12.0% | — |
| 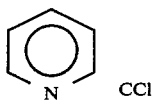 | 78.0% | 1.8% |
| 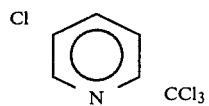 | 6.0% | — |
| 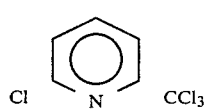 | — | 22.8% |
| 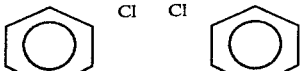 | — | 26.4% |
| 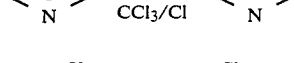 | — | — |
| 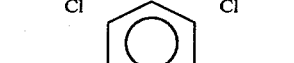 | — | 12.5% |
| 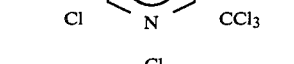 | 3.0% | 8.6% |
| 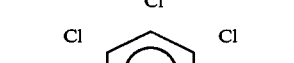 | — | 17.5% |

TABLE SEVEN

| Compound | Molar % of Initial Charge | Molar % after 5 hrs @ 220° C. | Molar % after 13 hrs @ 220° C. | Molar % after 21 hrs @ 220° C. |
|---|---|---|---|---|
| 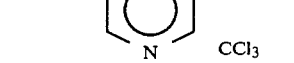 | 88.5% | 9.0% | — | — |
| 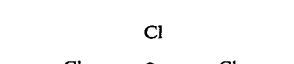 | 7.4% | 6.3% | — | — |
| 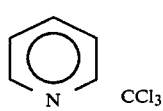 | — | 35.6% | 27.5% | 8.9% |
| 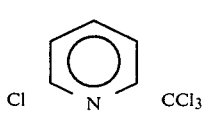 | — | 12.5% | 5.9% | 3.9% |

TABLE SEVEN-continued

| Compound | Molar % of Initial Charge | Molar % after 5 hrs @ 220° C. | Molar % after 13 hrs @ 220° C. | Molar % after 21 hrs @ 220° C. |
|---|---|---|---|---|
| 2,3,5-trichloro-6-(trichloromethyl)pyridine (Cl at 2,3,5; CCl₃ at 6) | — | 5.1% | 13.5% | 19.4% |
| 2,3,5,6-tetrachloro-(trichloromethyl)pyridine-like (Cl at 2,3,5,6; CCl₃) | — | 5.0% | 8.3% | 9.1% |
| pentachloropyridine (Cl at 2,3,4,5,6) | — | 7.9% | 15.6% | 19.7% |
| 2,3,5,6-tetrachloropyridine | — | 6.2% | 18.5% | 31.3% |

TABLE EIGHT

| Compound | Molar % of Initial Charge | Molar % after 32 hrs @ 150 C. | Molar % after 32 hrs @ 150° C. +76 hrs @ 175° C. |
|---|---|---|---|
| 2,3-dichloro-6-(trichloromethyl)pyridine (Cl at 2,3; CCl₃ at 6) | 92.7% | 85.5% | 26.8% |
| 2,3,5-trichloro-6-(trichloromethyl)pyridine | 0.3% | 1.7% | 19.2% |
| 2,3-dichloro-(trichloromethyl)pyridine isomer | 0.6% | 4.1% | 22.4% |
| 2,3,5,6-tetrachloro-(trichloromethyl)pyridine | — | 1.0% | 5.0% |
| 2,3,5,6-tetrachloropyridine | 1.0% | — | 3.3% |
| pentachloropyridine (2,3,4,5,6) | 1.0% | 2.3% | 13.8% |

TABLE NINE

| Compound | Molar % of Initial Charge | Molar % after 1% AlCl₃ 24 hrs @ 210° C. |
|---|---|---|
| 2,6-dichloro-(trichloromethyl)pyridine | 96.2% | 12.5% |
| 2,3,6-trichloro-(trichloromethyl)pyridine | 1.6% | 26.9% |
| 2,3,5,6-tetrachloropyridine | 0.4% | 50.5% |

TABLE TEN

| Compound | Molar % of Initial Charge | Molar % after 10 hrs @ 210° C. | Molar % after 32 hrs @ 210° C. |
|---|---|---|---|
| 3,4,6-trichloro-2-(trichloromethyl)pyridine (Cl at 3,4,6; CCl$_3$ at 2) | 96.2% | 73.5% | 37.4% |
| 3,4,5,6-tetrachloro-2-(trichloromethyl)pyridine | 1.6% | 10.3% | 18.7% |
| pentachloropyridine | 0.4% | 3.1% | 17.8% |

TABLE ELEVEN

| Compound | Molar % of Initial Charge | Molar % after 26 hrs @ 210° C. |
|---|---|---|
| 3,4,6-trichloro-2-(trichloromethyl)pyridine | 96.2% | 35.8% |
| 3,4,5,6-tetrachloro-2-(trichloromethyl)pyridine | 1.6% | 22.6% |
| pentachloropyridine | 0.4% | 22.0% |

As will be understood the chlorination process of the present invention can be performed in a multi-stage reactor, continuous system in which the total residence time during chlorination is controlled as a function of temperature to optimize the yield of 3,4,5,6-tetrachloro-2-trichloromethyl pyridine.

What is claimed is:

1. The process of producing a polychloro pyridine reaction product rich in 3,4,5,6-tetrachloro-2-trichloromethyl pyridine, said process comprising:
    (a) charging a reactor means with an initial charge which contains 3,4,5-trichloro-2-trichloromethyl pyridine;
    (b) adding ferric chloride catalyst to such initial charge, in the amount of at least about 3% by weight relative to the initial charge;
    (c) while maintaining the catalyzed charge in the reactor at a temperature in the range of from about 170° C. to about 220° C., sparging chlorine through the charge at a rate sufficient to maintain at least 50% excess chlorine in the gases from the reactor; and
    (d) continuing chlorine addition and heating of the charge under the indicated conditions until substantial conversion of the charge to 3,4,5,6-tetrachloro-2-trichloromethyl pyridine occurs.

2. The process of claim 1, further comprising removing the reaction mass from the reactor and separating 3,4,5,6-tetrachloro-2-trichloromethyl pyridine or its hydrolysis product 3,4,5,6-tetrachloro picolinic acid from the other chlorinated components of the reaction mass.

3. The process of claim 1, wherein the concentration of the ferric chloride catalyst in the initial charge is at least about 3% by weight, the reaction temperature is in the range of about 200° C. to 210° C., and the reaction is continued until the molar yield of 3,4,5,6-tetrachloro-2-trichloromethyl pyridine, based on conversion of 3,4,5-trichloro-2-trichloromethyl pyridine, is at least about 65%.

4. The process of claim 3, further comprising removing the reaction mass from the reactor and separating 3,4,5,6-tetrachloro-2-trichloromethyl pyridine or its hydrolysis product 3,4,5,6-tetrachloro picolinic acid from the other chlorinated components of the reaction mass.

* * * * *